United States Patent [19]

Coulter et al.

[11] Patent Number: 4,751,828
[45] Date of Patent: Jun. 21, 1988

[54] FREEZING APPARATUS FOR BIOLOGICAL TISSUE

[75] Inventors: H. David Coulter, New York, N.Y.; Wayne E. Schober, Minneapolis, Minn.

[73] Assignee: Regents of the University of Minnesota, Minneapolis, Minn.

[21] Appl. No.: 87,896

[22] Filed: Aug. 21, 1987

[51] Int. Cl.⁴ .............................................. F25B 19/00
[52] U.S. Cl. ..................................... 62/514 R; 62/62; 62/78
[58] Field of Search ............... 62/78, 514 R; 419/719, 419/720; 72/433, 434, 443; 83/613, 630, 626, 632; 267/137, 139; 188/72.1, 72.9, 72.6

[56] References Cited

U.S. PATENT DOCUMENTS

| | | | |
|---|---|---|---|
| 170,868 | 12/1875 | Lusted | 72/434 |
| 1,540,690 | 6/1925 | Friedman et al. | 72/434 |
| 3,902,390 | 9/1975 | Darbo | 83/170 |
| 4,017,983 | 4/1977 | Fraser | 34/92 |
| 4,197,658 | 4/1980 | Fraser | 34/92 |
| 4,232,453 | 11/1980 | Edelmann | 34/92 |
| 4,314,459 | 2/1982 | Rivoire | 62/514 R |
| 4,388,814 | 6/1983 | Schilling | 62/62 |
| 4,489,569 | 12/1984 | Sitte | 62/514 R |
| 4,563,883 | 1/1986 | Sitte | 62/514 R |

Primary Examiner—Steven E. Warner
Attorney, Agent, or Firm—Kinney & Lange

[57] ABSTRACT

A freezing apparatus for bringing samples of biological tissue in contact with a block of sapphire that is chilled to 15° K. has a toggle linkage that controls movement of a plunger carrying a biological tissue sample into contact with a cold surface of sapphire, and minimizes rebound by slowing the rate of approach of the tissue sample toward the cold surface to a velocity of substantially zero at contact. An outer box of plexiglass is used to limit the formation of condensates on the surface of the sapphire, and the specimen carrier includes a miniature moist chamber that protects the specimen from drying before moving it toward the surface. The moist chamber is removed just before operation of the freezing apparatus. The toggle linkage provides repeatability of results with minimum setup time between insertion of samples, and substantially reduces rebounding and vibration that retards the rate of freezing of the specimen.

17 Claims, 2 Drawing Sheets

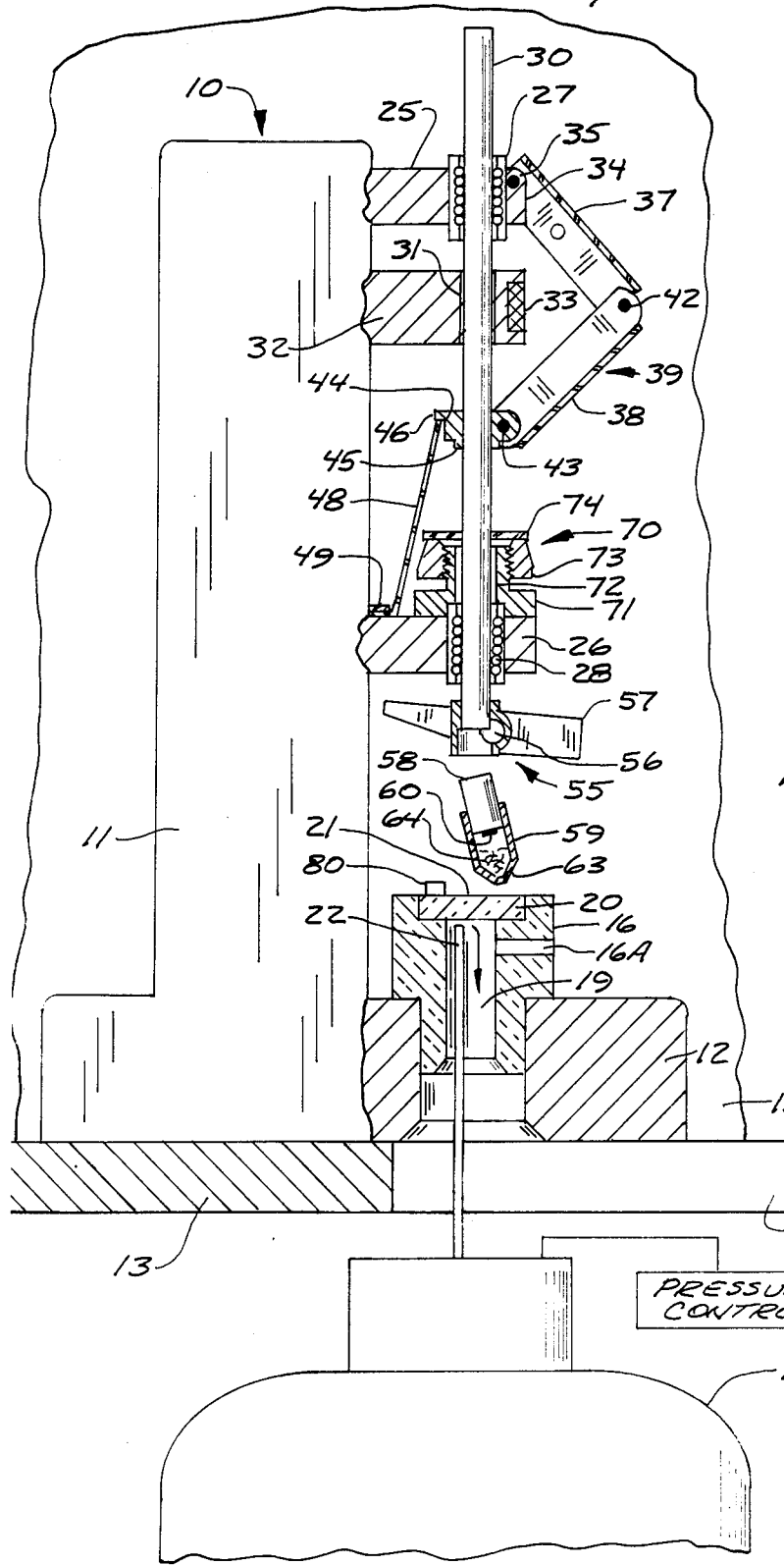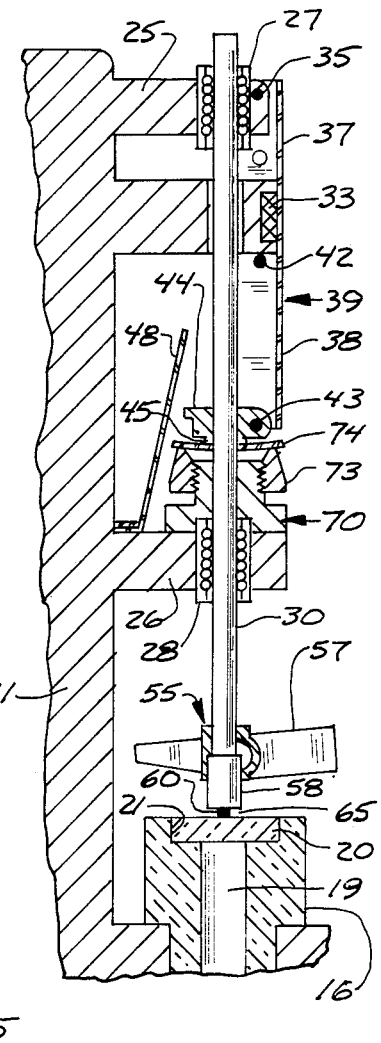
FIG. 2
FIG. 3

FREEZING APPARATUS FOR BIOLOGICAL TISSUE

This invention was made using funds from grants by the National Science Foundation and the National Institute of Health. The United States government has certain rights to this invention.

BACKGROUND OF THE INVENTION

1. Field of the Invention

The present invention relates to a freezing apparatus for substantially instantaneously freezing biological tissue samples for microscopic examination of such specimens.

2. Description of the Prior Art

Metal blocks cooled with liquid nitrogen or liquid helium have been used to freeze tissue samples for electron microscopy. In prior methods, a tissue sample has been placed on the end of a supporting rod and dropped onto a freezing block, which also served as a stop for the rod. Measures were taken to try to prevent the tissue from rebounding from the freezing surface after its initial contact. Even a millisecond bounce retards the rate of freezing of the sample sufficiently to cause ice crystal formation in the sample.

U.S. Pat. No. 4,563,883 illustrates an immersing device that has an injector which immerses a specimen in a cryogenic cooling liquid at a predetermined velocity. The injector is rotated before the vertical movement ends, to promote heat transfer from the specimen. This requires complete immersion, while the present system utilizes a cold sapphire plate which the specimen contacts for immediate freezing. U.S. Pat. No. 4,489,569 also shows a system for immersing a biological specimen in a cryogen for freezing. This, too, uses a submersion technique, including a plunger that is slidably mounted above the cryogen, and which can be manually depressed for injecting a sample and a sample holder into the cryogen.

After the samples have been frozen, they are subsequently treated for light or electron microscopic examination.

SUMMARY OF THE INVENTION

The present invention relates to a device for freezing biological samples uniformly, and quickly enough to avoid formation of ice crystals in the sample so when examined under a microscope, the tissue construction is representative of the condition of the tissue before freezing. The device utilizes a block having a cold surface that is maintained at a desired low temperature by constantly bathing the bottom of the block with liquid helium or other suitable cryogen, and quickly placing a specimen against the surface while preventing rebound so that the specimen is frozen immediately and without ice crystal formation.

The freezing apparatus comprises a base that is mounted above a Dewar flask containing liquid helium. The base has an insulated mounting block for mounting a sapphire block or disc. A specimen is mounted onto a millipore filter layer fixed to the lower end of a specimen carrier. The specimen carrier is placed into a chuck that is mounted onto a slidable rod directly aligned with the cold surface of the sapphire block. The slidable rod is spring loaded and controlled through the use of a toggle linkage to move the rod linearly toward the sapphire block. The toggle linkage slows the rate of approach of the specimen to the cold surface to a velocity of zero at the time the specimen approaches and touches the cold surface. The toggle linkage is held in its extended position with the specimen contacting the cold surface by a permanent magnet to prevent the rod and the specimen it carries from rebounding from the cold surface.

In the form shown, an adjustable, Belleville spring stop retards the velocity of the plunger carrying the specimen as the plunger end approaches the cold surface and the toggle approaches its straightened-out position. The spring also takes up any play in the pivot pins of the toggle linkage to avoid unwanted movement in the linkage.

The frame and base and other components are placed in an outer plexiglass glove box to limit the formation of condensate on the surface of the sapphire block and shield it from the atmosphere. Forceps can be used for inserting and removing the specimen and specimen carrier with respect to the chuck on the sliding plunger. A base below the glove box can have a hole, through which the forceps are manipulated.

The specimen also can be maintained at a proper moisture level by encapsuling the specimen carrier and specimen in a small polyethelene capsule sold under the trademark "BEEM" with a small amount of wet tissue paper in the bottom. The capsule is placed over the specimen carrier to make a miniature moist chamber for the specimen. The capsule is removed just before the toggle linkage is actuated for plunging the specimen to the cold surface. The various components for triggering the operation are operated through the gloves of the glove box.

BRIEF DESCRIPTION OF THE DRAWINGS

FIG. 2 is a vertical sectional view of the device of FIG. 1; and

FIG. 3 is a fragmentary vertical sectional view showing the specimen contacting a cold surface for freezing.

DETAILED DESCRIPTION OF THE PREFERRED EMBODIMENTS

Figure 1:
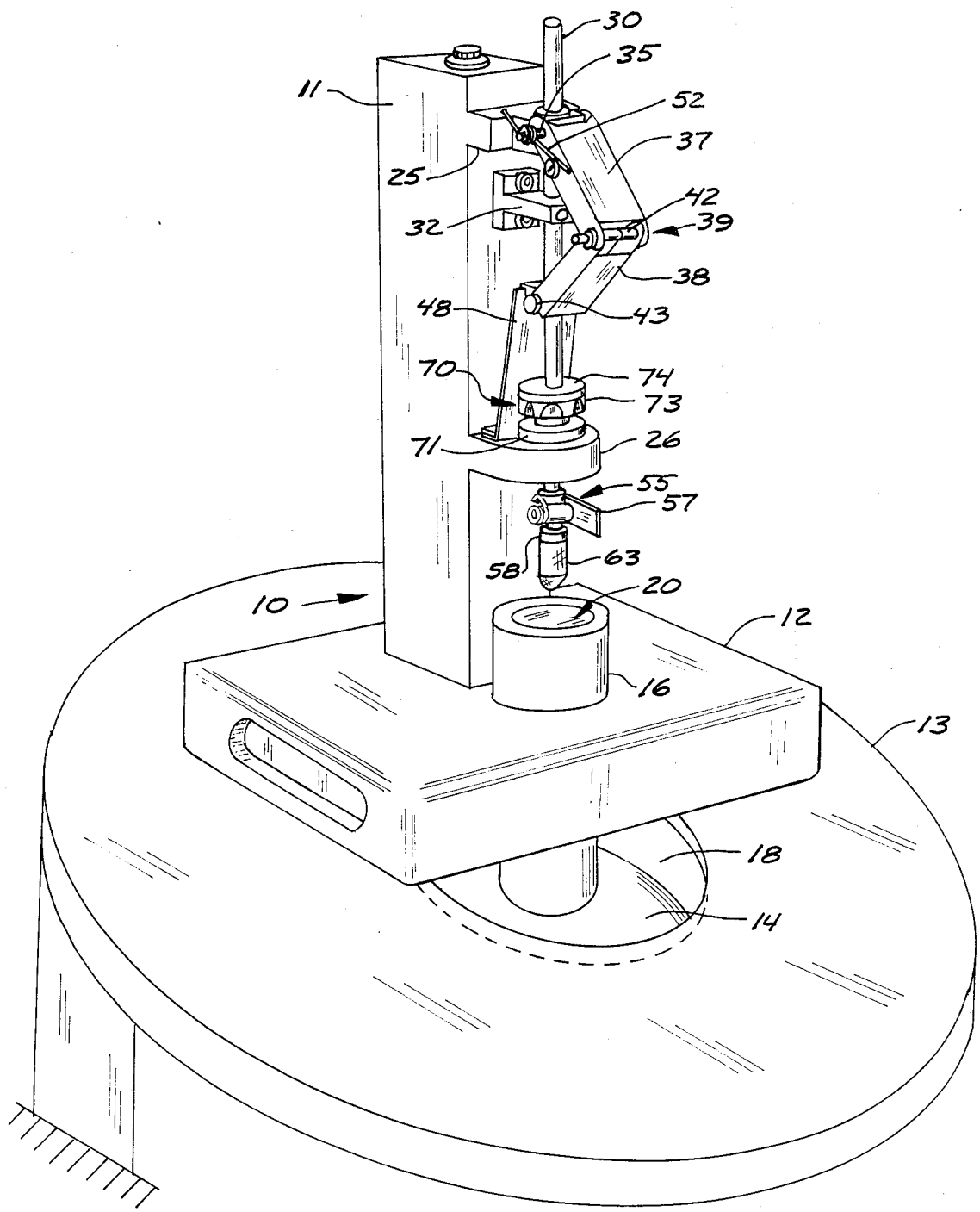
FIG. 1 is a perspective view of a freezer apparatus for biological tissue made according to the present invention, with an outer housing removed for sake of clarity.

Referring to FIG. 1, the freezing apparatus indicated generally at 10 comprises an upright support 11, that is mounted onto a base 12. The base 12 is supported on top of a thick disc of plexiglass 13 that is in turn supported in a suitable manner above a 30 liter liquid helium Dewar flask shown only schematically at 14, such as that made by Minnesota Valley Engineering, of New Prague, Minn. A plexiglass glove box which is indicated generally at 15 is supported on top of the disc 13. The glove box 15 encloses the pedestal 11 and it supported components. The glove box has interior gloves for manipulating the freezer apparatus from the exterior of the glove box as is well known.

As will be explained, the cryogen, comprising liquid helium, is transferred to provide a cold, known temperature to a surface, against which the tissue sample will be placed for freezing.

The base 12 has a fiberglass insulating cylindrical sleeve 16 fitted into a passageway or opening 17. The opening 17 aligns with a portion of a large opening 18 in the plexiglass disc 13. A sapphire block indicated generally at 20 is mounted on the upper surface of the insulating fiberglass sleeve 16. The sapphire block has an upper surface 21. The sleeve 16 has a central passageway 19 in which a helium transfer tube 22 is mounted. Helium is expelled through the tube 22 by use of a control shown schematically at 23 that regulates the pressure on the interior of the Dewar flask 14 to force helium out the transfer tube 22 at a desired rate. The transfer tube 22 is a double-walled tube, with a vacuum between the walls, and the tube has an open end positioned close to the undersurface of the sapphire block 20, and as can be seen the upper surface 21 of the sapphire block faces upwardly and is adjacent to the support column 11.

The support column 11 has an upper bearing support 25, and a lower bearing support 26 mounted thereon. The bearing supports extend outwardly and mount linear bearings 27 and 28, respectively, of suitable design, and these bearings in turn slidably mount a plunger shaft 30 that is axially aligned with the center of the upper surface 21 of the sapphire block 20. The plunger shaft 30 is positioned above the surface 21 as can be seen in FIG. 2. The plunger shaft 30 also passes through a clearance opening 31 in a laterally extending support member 32 that in turn carries a permanent magnet 33 on its outer surface, for purposes which will be explained.

The upper bearing support 25 has an outwardly extending portion 34 through which a pin 35 passes. Pin 35 forms a first pivot pin for a first end of the upper link portion 37 of a toggle linkage assembly 39. The lower link portion 38 of the toggle linkage assembly 39 is pivotally connected with a bolt or pin 42 to the second end of the upper link portion 37. The two link portions 37 and 38 will fold and form a toggle link. The lower end of the link portion 38 in turn is pivotally mounted with a suitable pivot pin or bolt 43 to a collar 44 that is mounted onto the plunger shaft 30, and which can be adjustably fixed in a desired axial position on the longitudinal axis of the plunger shaft 30. This adjustment can be done in any desired manner, such as using a split clamp collar, or a set screw, but the adjustability of the plunger 30 relative to the toggle linkage assembly 39 is important for proper adjustment and operation.

The collar 44 has a short neck 45 at its lower end that surrounds the plunger shaft 30. The collar 44 also has a lip 46 at its upper edge on the side thereof closely adjacent to the column 11. The lip 46 is of size to be engaged by and supported on a detent spring 48 that in turn is mounted with a suitable mounting clip 49 to the lower bearing support 26. The detent spring 48 is made so that it will support the collar 44, the plunger 30 and the toggle linkage assembly 39 in its partially folded or "cocked" position shown in FIG. 2 with the plunger 30 raised. A torsion spring 52 is used for urging the upper link portion 37 to pivot in a clockwise direction around the pin 35. The torsion spring 52, can be mounted as desired to the upper toggle link portion 37. The detent spring 48 has sufficient rigidity to hold the toggle linkage assembly 39 in its partially folded or cocked position shown in FIG. 2 with the plunger shaft 30 raised.

The lower end of the plunger shaft 30 has a chuck indicated generally at 55 thereon which is spring-loaded and adapted for holding a cylindrical aluminum specimen carrier 58 using a detent latch 56. A lever 57 can be used for actuating the chuck 55 in a known manner. The chuck is of size to receive and retain the specimen carrier 58. The specimen carrier 58 has a millipore filter 59 fixed at its lower end, and a sample of tissue 60 to be frozen is placed on the millipore filter.

In FIG. 2, the specimen carrier 58 is shown as it is being installed in the chuck 55, and as shown, a polyethylene cylindrical capsule 63 is placed over the specimen 60 and the lower end of the specimen carrier 58. The cylindrical capsule 63 is made so that it fits tightly on the carrier 58. The capsule 63 has a closed lower end and it has a suitable amount of wet tissue paper indicated at 64 to maintain the specimen 60 moist. This capsule 63, which is sold under the trademark BEEM, forms a miniature moist chamber for the tissue sample.

A portion of opening 18 in the disc or panel 13 is positioned ahead of the base 12 and this opening is accessible from the lower side. The opening 18 is of size and is positioned so that an assistant can pass the specimen carrier (with the specimen 60 and capsule 63 in place) and through the opening to an operator whose hands are in the gloves of the glove box and who can then seat the specimen carrier into the chuck 55.

The plunger shaft 30 is adjusted prior to use so that is reaches a fixed, known position when the toggle linkage assembly straigtens out to its extended nearly straight line position as shown in FIG. 2, where the pivot points of pivot bolt or pin, 42 is close to the plane defined by the axis of pivot bolts 35 and 43. It is desirable that the linkage does not go completely "on center" or lock. It should be noted that as the axis of pin 42 approaches a reference plane defined by the axis of pins 43 and 35, the additional axial movement of shaft 30 is very small. Thus, the pin 42 can be spaced slightly from the reference plane without causing any substantial effect on the position of the specimen. By adjusting the collar 44, the minimum clearance indicated generally at 65 in FIG. 3 between the end of the specimen carrier 58, and the upper surface 21 of the sapphire block can be controlled. This minimum clearance is with specimen carrier 58 fully seated in the chuck 55 and the toggle linkage assembly 39 extended to an almost straight line position. This clearance will be selected so that the specimen being carried will not be crushed, but will be forced into intimate contact with the surface 21 for freezing. This clearance would be in the range of 0.35 mm. That is, with the millipore filter fixed on the end of the specimen carrier, the distance from the millipore filter to the surface 21 of the sapphire block would be the set amount so that the specimen would firmly contact the sapphire surface, but would not be crushed.

In order to absorb kinetic energy during the last portion of the movement of the toggle linkage assembly and plunger shaft as the linkage assembly 39 closely approaches its 180° (straight line) position, an adjustable stop illustrated generally at 70 is used. The stop 70 comprises a sleeve base 71 that is mounted to the bearing support 26. The sleeve base 71 has a clearance opening 72 through which the plunger shaft 30 will pass, and at its upper end there is a threaded collar 73 mounted onto a threaded neck of the base 71. Collar 73 in turn supports the outer annular edge of a thin spring steel washer (Belleville spring) 74. The washer 74 has a central opening through which the plunger shaft 30 extends. The edge of the opening in the washer 74 is spaced closely from the plunger 30. The washer 74 is made of spring material, and is positioned so that the neck 45 of the collar 44 will engage the washer before the toggle linkage assembly 39 reaches its extended position. Continued movement of the plunger shaft deflects the center of the washer 74 downwardly as shown in FIG. 3. Spring washer 74 absorbs kinetic energy, and because the plunger shaft 30 is slowing in velocity due to the action of the toggle linkage assembly 39 during the last few degrees of pivoting of the toggle linds themselves relative to each other, an adjustment can be made so that the collar 73 will position the spring washer 74 to insure that the toggle linkage assembly 39 can reach its extended position as shown in FIG. 3 and the spring washer will absorb energy to reduce the tendancy to have any vibration of the plunger shaft when the plunger shaft 30 reaches its lowest position. Also, the spring 74 loads the pivot pins for the linkage to take up any clearance and prevent them from vibrating or rattling. Adjustment of the spring tension can be made to fine-tune the system also to avoid any bounce or rebound of the linkage or of the specimen after it first engages the cold surface 21 of the sapphire block 20.

When the toggle linkage assembly 39 is in its extended position or its plunged position, the magnet 33 will engage the base wall of the link portion 37 (the link portions 37 and 38 are channel-shaped) and will hold the link portion 37 from rebounding, and thus keep the toggle linkage assembly essentially straight so that the plunger shaft 30 is held positively in its extended position with the specimen 60 engaging the surface 21 of the sapphire block 20 for instantaneously freezing the specimen.

In operation, liquid helium in the Dewar flask 14 is passed through the tube 22, which is about 1 mm in internal diameter and spaced approximately 2 mm from the lower surface of the sapphire block 20. A couple of small openings such as that shown at 16A in the fiberglass block 16 provide for vapor to escape into the housing formed by the glove box 15, to replace the atmosphere. The sapphire block 20 is cooled by the helium striking its bottom surface to a temperature of about 15° K. The opening 18 in the plexiglass base plate 13 also permits helium vapors to escape. The transfer tube 22 provides a 1 mm stream of liquid helium to the lower surface of the sapphire block 20. The sapphire block 20 is approximately one quarter inch in thickness, and is insulated from the frame column 11 and base 12 by the cylinder of fiberglass 16.

The plunger shaft 30 is put in its retracted or raised position, and held in the position against the action of the torsion springs 52 by the detent spring lever 48, engaging detent lip 46. The toggle linkage assembly is in approximately a 90° position, that is, the two link positions 37 and 38 define an included angel of 90° in the retracted position. The collar 44 which connects the link portion 38 and thus the toggle linkage assembly to the plunger shaft 30 is previously adjusted to give the desired clearance between the end of the specimen carrier 58 and the surface 21. The specimen carrier 58 with a specimen 60 on its lower end, and with the outer capsule 63 forming the moist chamber in place is put into the chuck 55 using forceps acting through the provided opening 18 in the base 13. The specimen is then loaded in place, and can be left in the chuck for a short while with the plunger shaft 30 in its retracted position without damage.

The surface 21 of the sapphire block is scraped of any condensation using tools operated throguh the gloves of the glove box. The flow of helium can be controlled by regulating pressure on the liquid helium in the Dewar flask 14 to the desired level so that the temperature of surface 21 is maintained. This temperature can be sensed with a suitable sensing chip indicated schematically at 80, using a commercially available germanium chip. The temperature is stabilized before inserting the specimen and specimen carrier into the chuck. Thus, when the specimen carrier has been placed in the chuck, once the surface of the sapphire block 20 has been scraped, the capsule 63 forming the moist chamber is removed by an operator using the gloves of the glove box, and detent spring 48 is immediately released using the opposite hand from the one used for removing the capsule 63 from the specimen holder 58. The plunger shaft 30 will be accelerated toward the sapphire surface 21, as controlled by the toggle linkage assembly 39. The tissue specimen 60 will contact and freeze on the surface 21 of the sapphire block 20 in less than a second after removing the moist chamber formed by capsule 63.

The aluminum specimen carrier 58 and specimen 60 are left undisturbed for about ten seconds, after which the chuck 55 is released by moving the handle 57 suitably, to leave the aluminimum carrier and the specimen 60 upright on the cold surface 21 of the sapphire block.

Using forceps operated by an operator using the gloves of the glove box, the specimen carrier 58 and frozen specimen 60 are picked up and dropped into a styrofoam cup filled with liquid nitrogen held by an assistant below opening 18 and then stored. The tissue sample or specimen will be treated in a desired process which will prepare the specimen for examination. A drying process may be used using generally known techniques to dry the specimen and fix it with a suitable resin for examination.

The freezing apparatus thus is relatively simple to make, but is very reliable in operation by properly adjusting the position of the energy absorbing spring washer, and the lowermost position of the plunger shaft. Repeatable freezing results are obtained because the specimen does not rebound fron the cold surface 21 once it contacts it. The specimen is frozen quickly without formation of ice crystals in the specimen.

Although the present invention has been described with reference to preferred embodiments, workers skilled in the art will recognize that changes may be made in form and detail without departing from the spirit and scope of the invention.

What is claimed is:

1. An apparatus for treating specimens of tissue by bringing such specimens into contact with a surface, comprising:
   a base position to support the surface;
   a plunger slidably mounted with respect to said base for movement toward and away from said surface between first and second positions;
   means on said plunger on an end thereof facing the surface for supporting a specimen to be treated;
   mechanical linkage means for controlling movement of said plunger toward and away from said surface, said linkage means being operable to reduce the velocity of the plunger as it approaches the surface and the second position; and
   means for stopping the linkage means in a known position with the plunger in its second position and with a specimen supported by said plunger in contact with said surface.

2. The apparatus of claim 1 and means for latching said linkage means with the plunger in its second position.

3. The apparatus of claim 1 and a moist chamber comprising a capsule for enclosing a specimen mounted on said plunger, said capsule being removable before operating the plunger to move from its first to its second position before contacting said surface.

4. The apparatus of claim 1 wherein said base has an insulating sleeve mounted thereon, said surface comprising a cryogen cooled surface on a block of material, said block of material being mounted on said sleeve, and means for providing a liquid cryogen bath to a side of said block of material opposite from the surface contacted by the specimen when the plunger is in its second position.

5. The apparatus of claim 1 and means to apply a cryogen to cool the surface for freezing specimens contacting such surface.

6. The apparatus as specified in claim 1 wherein said linkage means comprises a toggle linkage assembly having a pair of pivoting link portions that move to a straight line position when the plunger is in its second position.

7. The apparatus of claim 6 wherein said toggle linkage assembly comprises first and second link portions that are pivotally mounted together at a center pivot, the first link portion also being pivotally mounted relative to said base, and said second link portion also being pivotally mounted with respect to said plunger, said plunger moving from its first position with the first and second link portions in a folded position where the included angle between the link portions is substantially less than 180°, to its second position wherein the included angle between the link portions is approaching substantially 180°.

8. The apparatus of claim 7 and a detent operable to hold said plunger in its first position, and spring means urging said toggle linkage assembly to move the first and second link portions to the second position.

9. The apparatus of claim 1 and means for absorbing energy of movement of said plunger as the plunger approaches its second position.

10. The apparatus of claim 9 and means for adjusting the means for absorbing energy relative to the plunger second position so that the means for absorbing energy is effective at a selected position of the plunger.

11. The apparatus of claim 9 wherein said means for absorbing energy comprises a spring washer surrounding said plunger, a collar on said plunger adapted to engage said spring washer shortly prior to the time the plunger reaches its second position.

12. An apparatus for treating samples of tissue by placing the sample into contact with a surface having a controlled temperature comprising:
   a frame member having an upright column portion;
   means for slidably mounting a plunger with respect to said upright column portion for movement along a plunger axis;
   bias means to urge said plunger in a first direction from a first retracted to a second position;
   means for providing a surface positioned generally transversely to the axis of the plunger in position to be adjacent an end of the plunger when the plunger is in its second position;
   linkage means for urging said plunger in a direction from its first retracted to its second position including an adjustable coupling member connected to said plunger for adjusting the position of the end portion of said plunger relative to the means for providing a surface;
   a releasable detent to hold said plunger in its retracted position, said linkage means having means for controlling the velocity of the plunger along the plunger axis as the plunger approaches its second position to be reduced from the velocity of the plunger during other portions of travel of the plunger from its first retracted to its second position; and
   means supporting a specimen to be treated on the end of said plunger adjacent said means for providing a surface, so that with the plunger in its second position the specimen firmly contacts a provided surface.

13. The apparatus of claim 12 including magnet means positioned adjacent to the linkage means to hold said linkage means in position where the plunger has reached its second position.

14. The apparatus of claim 12 wherein said means supporting a specimen comprises a specimen mounting cylinder, a chuck on said plunger for holding said cylinder, and a capsule adapted to fit over an end of said specimen mounting cylinder opposite from the chuck to provide an enclosed chamber surrounding a specimen on the specimen mounting cylinder prior to the time the plunger is moved from its first to its second positions.

15. The apparatus of claim 12 wherein said linkage means comprises a toggle linkage having first and second link portions, respectively, the first link portion having a first end pivotally mounted with respect to said frame, and a second end pivotally mounted to a first end of the second link position, said second link portion having a second end adjustably pivotally coupled to the plunger, whereby the pivotal connections of the second ends of said first and second link portions is close to a plane defined by the pivotal connection of the first ends of said link portions with the plunger in its second position.

16. The apparatus of claim 15 and spring means tending to urge at least one of said link portions toward a position wherein the pivotal connection between the link portions is closely spaced from a plane defined by the pivotal connections of the other ends of the link portions.

17. The apparatus of claim 16 wherein the means for providing a surface comprises a block of heat conducting material having a surface facing the plunger, and a source of liquid helium to bathe the block of heat conducting material on a surface opposite from the first mentioned surface on which a specimen is to be placed.

* * * * *